(12) United States Patent (10) Patent No.: US 12,138,078 B2
Zou (45) Date of Patent: Nov. 12, 2024

(54) MOBILE DEVICE AND CONTROL METHOD THEREOF

(71) Applicant: MediaTek Inc., Hsin-Chu (TW)

(72) Inventor: Teng-Feng Zou, Hsin-Chu (TW)

(73) Assignee: MEDIATEK INC., Hsinchu (TW)

( * ) Notice: Subject to any disclaimer, the term of this patent is extended or adjusted under 35 U.S.C. 154(b) by 0 days.

(21) Appl. No.: 18/193,828

(22) Filed: Mar. 31, 2023

(65) Prior Publication Data

US 2023/0240616 A1 Aug. 3, 2023

Related U.S. Application Data

(63) Continuation of application No. 15/693,557, filed on Sep. 1, 2017, now abandoned.

(Continued)

(51) Int. Cl.
*A61B 5/021* (2006.01)
*A61B 5/00* (2006.01)
*A61B 5/08* (2006.01)
*A61B 5/25* (2021.01)
*A61B 5/291* (2021.01)

(Continued)

(52) U.S. Cl.
CPC ............ *A61B 5/6898* (2013.01); *A61B 5/021* (2013.01); *A61B 5/0809* (2013.01); *A61B 5/25* (2021.01); *A61B 5/291* (2021.01); *A61B 5/6817* (2013.01); *A61B 5/7203* (2013.01); *G06F 1/1698* (2013.01); *H01R 13/6691* (2013.01); *H01R 13/70* (2013.01); *H04M 1/0274* (2013.01); *A61B 2560/0468* (2013.01);

*A61B 2562/0209* (2013.01); *A61B 2562/225* (2013.01); *A61B 2562/227* (2013.01); *H01R 24/58* (2013.01);

(Continued)

(58) Field of Classification Search
CPC .... A61B 5/6898; A61B 5/0404; A61B 5/0402
See application file for complete search history.

(56) References Cited

U.S. PATENT DOCUMENTS 9,089,270 B2 * 7/2015 Song ...................... H04M 1/05
2010/0210959 A1 8/2010 Karo
(Continued)

FOREIGN PATENT DOCUMENTS

CN 202409150 U 9/2012
CN 102866843 A 1/2013
(Continued)

OTHER PUBLICATIONS

Extended European Search Report for European Application No. 17191139.9 dated Jan. 19, 2018.
(Continued)

*Primary Examiner* — George R Evanisko
(74) *Attorney, Agent, or Firm* — Winston Hsu (57) ABSTRACT

A mobile device includes a connector, an audio generator, a biological signal processor, a switch element, and a controller. The switch element has a first terminal and a second terminal. The first terminal of the switch element is coupled to the connector, and the second terminal of the switch element is selectively coupled to either the audio generator or the biological signal processor according to a control signal. The controller is coupled to the audio generator and the biological signal processor, and is configured to generate the control signal.

4 Claims, 9 Drawing Sheets

Related U.S. Application Data (60) Provisional application No. 62/394,287, filed on Sep. 14, 2016.

(51) Int. Cl.

| | | |
|---|---|---|
| *G06F 1/16* | (2006.01) | |
| *H01R 13/66* | (2006.01) | |
| *H01R 13/70* | (2006.01) | |
| *H04M 1/02* | (2006.01) | |
| H01R 24/58 | (2011.01) | |
| H01R 105/00 | (2006.01) | |

(52) U.S. Cl.
CPC ..... *H01R 2105/00* (2013.01); *H04M 2250/12* (2013.01)

(56) References Cited

U.S. PATENT DOCUMENTS

| | | | | |
|---|---|---|---|---|
| 2012/0123222 | A1* | 5/2012 | Chen | A61B 5/14532 600/301 |
| 2013/0005303 | A1* | 1/2013 | Song | A61B 5/02438 455/411 |
| 2014/0073887 | A1 | 3/2014 | Petersen et al. | |
| 2014/0155708 | A1 | 6/2014 | Petersen et al. | |
| 2014/0368355 | A1* | 12/2014 | Chung | G08C 23/02 340/870.07 |
| 2016/0286297 | A1* | 9/2016 | Wang | H04R 1/1016 |
| 2018/0070881 | A1 | 3/2018 | Zou | |

FOREIGN PATENT DOCUMENTS

| | | |
|---|---|---|
| CN | 103297887 A | 9/2013 |
| CN | 104202691 A | 12/2014 |
| CN | 104797188 A | 7/2015 |
| CN | 105338893 A | 2/2016 |
| CN | 205544410 U | 8/2016 |
| WO | WO 2016/029633 A1 | 3/2016 |

OTHER PUBLICATIONS

[No Author Listed], Response definition. Oxford English Dictionary. Mar. 2022. 10 pages.

[No Author Listed], Response. The American Heritage Dictionary of the English Language. 2022. 5 pages.

Hsu et al., Robust signal synthesis of the 12-lead ECG using 3-lead wireless ECG systems. 2014 IEEE International Conference on Communications (ICC) Jun. 10, 2014:3517-22.

* cited by examiner

MOBILE DEVICE AND CONTROL METHOD THEREOF

CROSS REFERENCE TO RELATED APPLICATIONS

This Application is a Continuation of U.S. application Ser. No. 15/693,557, filed Sep. 1, 2017, entitled "MOBILE DEVICE AND CONTROL METHOD THEREOF", which claims the benefit of U.S. Provisional Application No. 62/394,287, filed Sep. 14, 2016, the entirety of each of which is incorporated by reference herein.

BACKGROUND OF THE INVENTION

Field of the Invention

The disclosure generally relates to a mobile device, and more specifically, to a mobile device for receiving and processing a biological signal.

Description of the Related Art

As technology advances, mobile electronic devices are playing an increasingly important role in people's lives. Some mobile electronic devices, such as smart sports bracelets, can automatically collect biological information from users and transmit it to other devices for further processing. However, the biological information may become distorted because of a bad transmission path. Accordingly, there is a need to design a novel solution for solving the aforementioned problem.

BRIEF SUMMARY OF THE INVENTION

In a preferred embodiment, the disclosure is directed to a mobile device including a connector, an audio generator, a biological signal processor, a switch element, and a controller. The switch element has a first terminal and a second terminal. The first terminal of the switch element is coupled to the connector, and the second terminal of the switch element is selectively coupled to either the audio generator or the biological signal processor according to a control signal. The controller is coupled to the audio generator and the biological signal processor, and is configured to generate the control signal.

In some embodiments, when an external device is coupled to the connector, the switch element initially couples the connector to the biological signal processor.

In some embodiments, the controller controls a switching operation of the switch element according to information from the external device.

In some embodiments, the external device is an external earphone or an external sensor.

In some embodiments, the external sensor is an external electrode.

In some embodiments, if the connector receives a first biological signal from the external device, the first biological signal is transmitted through the switch element to the biological signal processor, such that the biological signal processor processes the first biological signal.

In some embodiments, if the connector does not receive any biological signal from the external device, the switch element changes its switching operation and couples the connector to the audio generator, instead of the biological signal processor.

In some embodiments, the mobile device further includes a housing and a plurality of sensors. The sensors are embedded in the housing, and are coupled to the biological signal processor.

In some embodiments, the sensors are electrodes.

In some embodiments, if no external device is coupled to the connector or if the connector does not receive any biological signal from the external device, the biological signal processor tries to receive and process a second biological signal from the sensors.

In another preferred embodiment, the disclosure is directed to a method including the steps of: providing a mobile device, wherein the mobile device includes a connector, an audio generator, a biological signal processor, a switch element, and a controller, and wherein the controller is coupled to the audio generator and the biological signal processor; generating a control signal by the controller; and coupling the connector to either the audio generator or the biological signal processor by the switch element according to the control signal.

In some embodiments, the method further includes: when an external device is coupled to the connector, initially coupling the connector to the biological signal processor by the switch element.

In some embodiments, the method further includes: controlling a switching operation of the switch element by the controller according to information from the external device.

In some embodiments, the method further includes: if the connector receives a first biological signal from the external device, transmitting the first biological signal through the switch element to the biological signal processor, and processing the first biological signal by the biological signal processor.

In some embodiments, the method further includes: if the connector does not receive any biological signal from the external device, coupling the connector to the audio generator, instead of the biological signal processor, by the switch element.

In some embodiments, the method further includes: if no external device is coupled to the connector or if the connector does not receive any biological signal from the external device, trying to receive and process a second biological signal from the sensors by the biological signal processor.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

In order to illustrate the purposes, features and advantages of the invention, the embodiments and figures of the invention will be described in detail as follows.

Certain terms are used throughout the description and following claims to refer to particular components. As one skilled in the art will appreciate, manufacturers may refer to a component by different names. This document does not intend to distinguish between components that differ in name but not function. In the following description and in the claims, the terms "include" and "comprise" are used in an open-ended fashion, and thus should be interpreted to mean "include, but not limited to . . . ". The term "substantially" means the value is within an acceptable error range. One skilled in the art can solve the technical problem within a predetermined error range and achieve the proposed technical performance. Also, the term "couple" is intended to mean either an indirect or direct electrical connection. Accordingly, if one device is coupled to another device, that connection may be through a direct electrical connection, or through an indirect electrical connection via other devices and connections.

Figure 1:
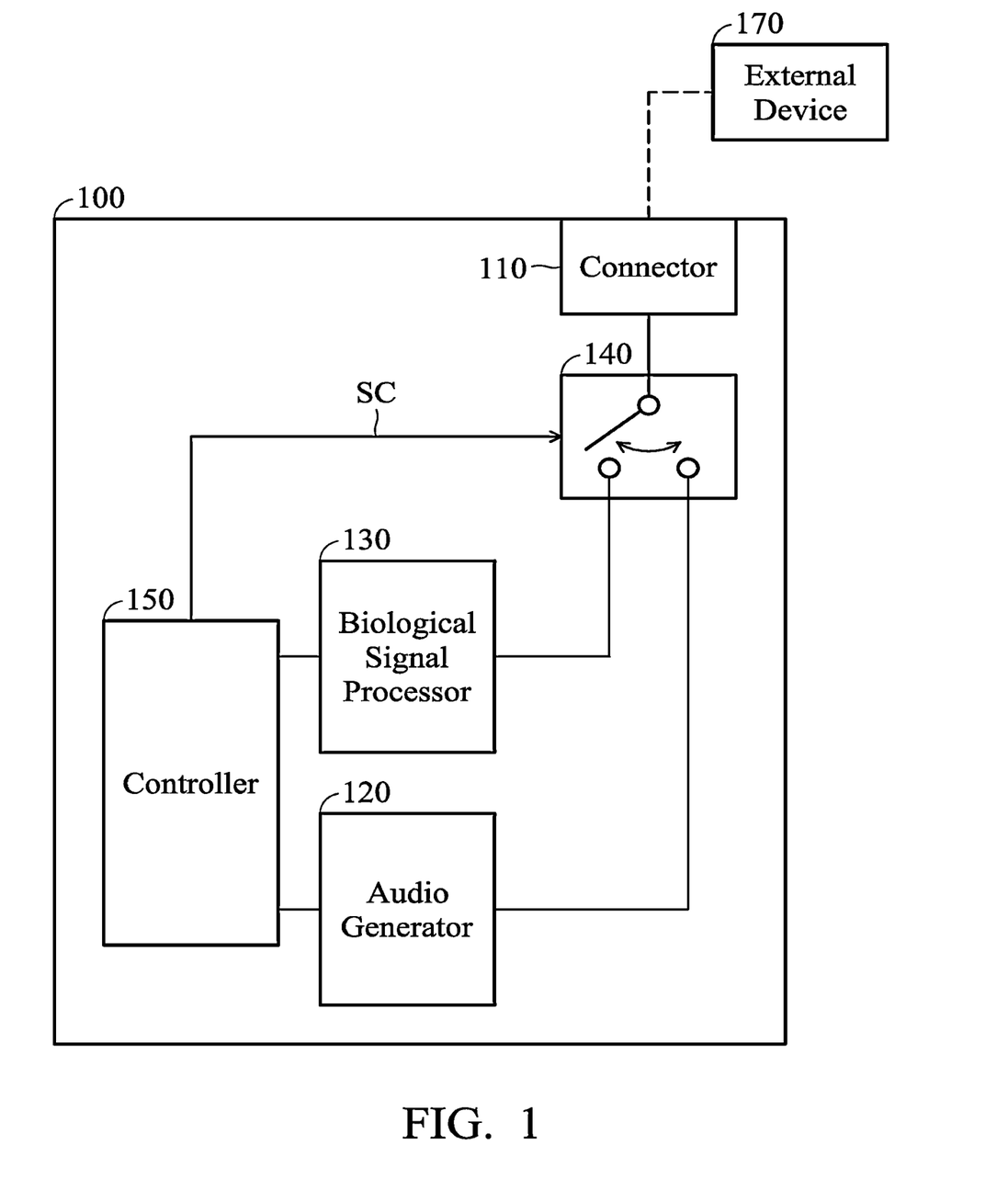
FIG. 1 is a diagram of a mobile device according to an embodiment of the invention.

FIG. 1 is a diagram of a mobile device 100 according to an embodiment of the invention. For example, the mobile device 100 may be a smartphone, a tablet computer, or a notebook computer. As shown in FIG. 1, examples of the mobile device 100 include a connector 110, an audio generator 120, a biological signal processor 130, a switch element 140, and a controller 150. The connector 110 may be selectively coupled to an external device 170. For example, the connector 110 may be an earphone socket, but it is not limited thereto. Alternatively, the connector 110 may be a USB (Universal Serial Bus) socket, a micro-USB socket, or a USB type-C socket. The audio generator 120 is configured to generate and output an audio signal. The biological signal processor 130 is configured to receive and process a biological signal. The switch element 140 may be an SPDT (Single Port Double Throw) switch. The switch element 140 has a first terminal and a second terminal. The first terminal of the switch element 140 is coupled to the connector 110, and the second terminal of the switch element 140 is selectively coupled to either the audio generator 120 or the biological signal processor 130 according to a control signal SC. The controller 150 may be a control circuit, and it may be integrated with the audio generator 120 so as to form a single control chip. The controller 150 is coupled to the audio generator 120 and the biological signal processor 130, and is configured to generate the control signal SC for controlling the switch element 140. For example, the controller 150 may include any custom-made or commercially available processor, a central processing unit (CPU) or an auxiliary processor among several processors associated with the mobile device 100, a semiconductor based microprocessor (in the form of a microchip), a macroprocessor, one or more application-specific integrated circuits (ASICs), a plurality of suitably configured digital logic gates, and other well-known electrical configurations comprising discrete elements both individually and in various combinations to coordinate the overall operation of the computing system.

In some embodiments, when the external device 170 is coupled to the connector 110, the switch element 140 can initially couple the connector 110 to the biological signal processor 130. Then, the controller 150 can maintain or change the switching operation of the switch element 140 according to information from the external device 170. For example, the aforementioned information may include the type of the external device 170, or signals output from the external device 170. The following embodiments describe the detailed operation of the mobile device 100. It should be noted these embodiments and figures are just exemplary, rather than the restricted limitations of the invention.

Figure 2:
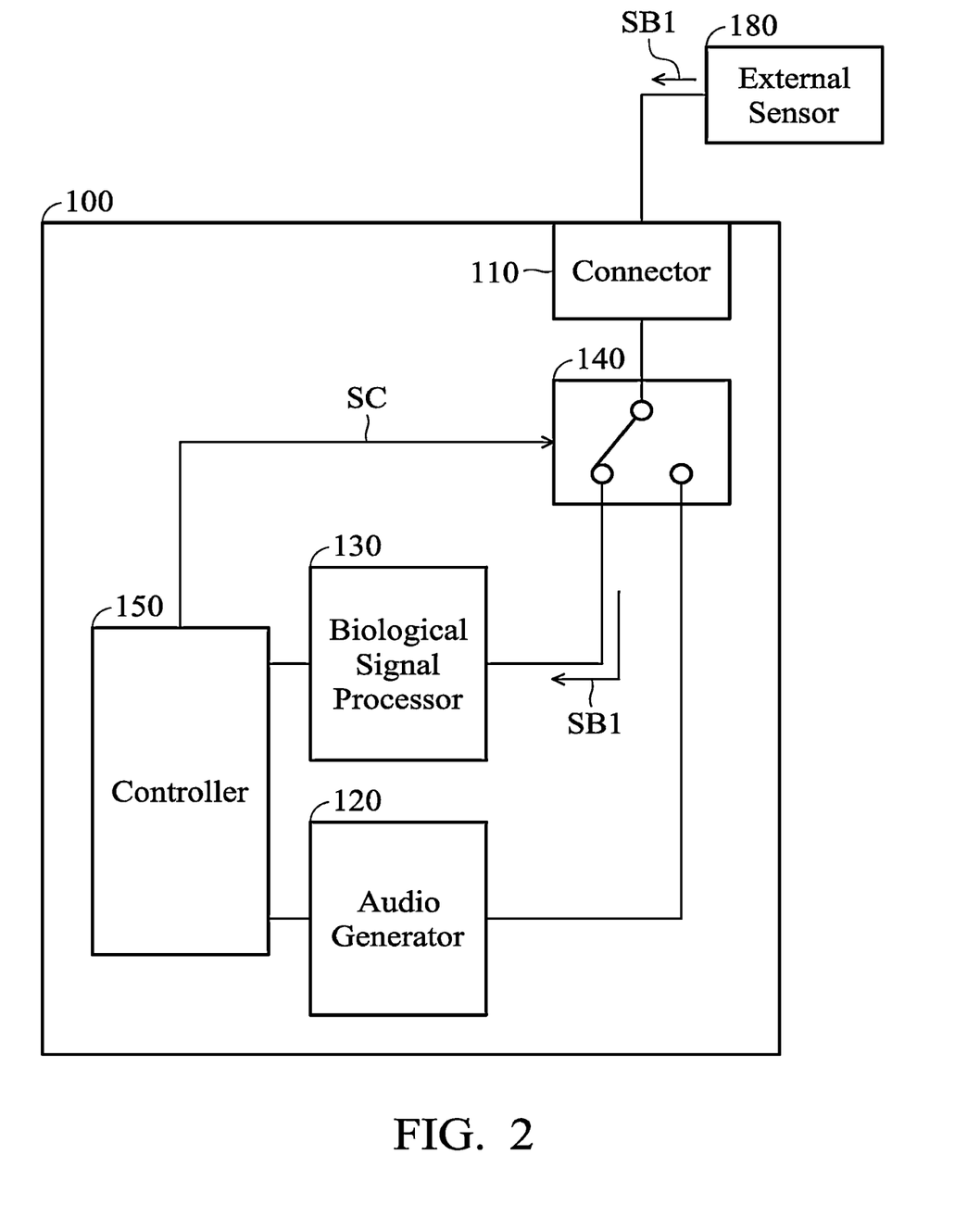
FIG. 2 is a diagram of a mobile device coupled to an external sensor according to an embodiment of the invention.

FIG. 2 is a diagram of the mobile device 100 coupled to an external sensor 180 according to an embodiment of the invention. In the embodiment of FIG. 2, the aforementioned external device 170 is an external sensor 180, and the external sensor 180 is coupled to the connector 110 of the mobile device 100. The external sensor 180 may collect a variety of biological information from a user, so as to generate a first biological signal SB1. If the connector 110 receives the first biological signal SB1 from the external sensor 180, the switch element 140 will maintain its initial switching operation (i.e., the switch element 140 selects the biological signal processor 130), and the first biological signal SB1 will be transmitted through the switch element 140 to the biological signal processor 130, such that the biological signal processor 130 can process the first biological signal SB1. For example, the first biological signal SB1 may be a heartbeat signal, and the biological signal processor 130 can process the first biological signal SB1 and then output an electrocardiogram signal. The electrocardiogram signal may be displayed on a display device (not shown), or may be analyzed further by an application program of the mobile device 100. However, the invention is not limited to the above. In alternative embodiments, the first biological signal SB1 may be a respiratory signal, a brain wave signal, or blood pressure, and the biological signal processor 130 can also process it and perform a corresponding operation.

Figure 3:
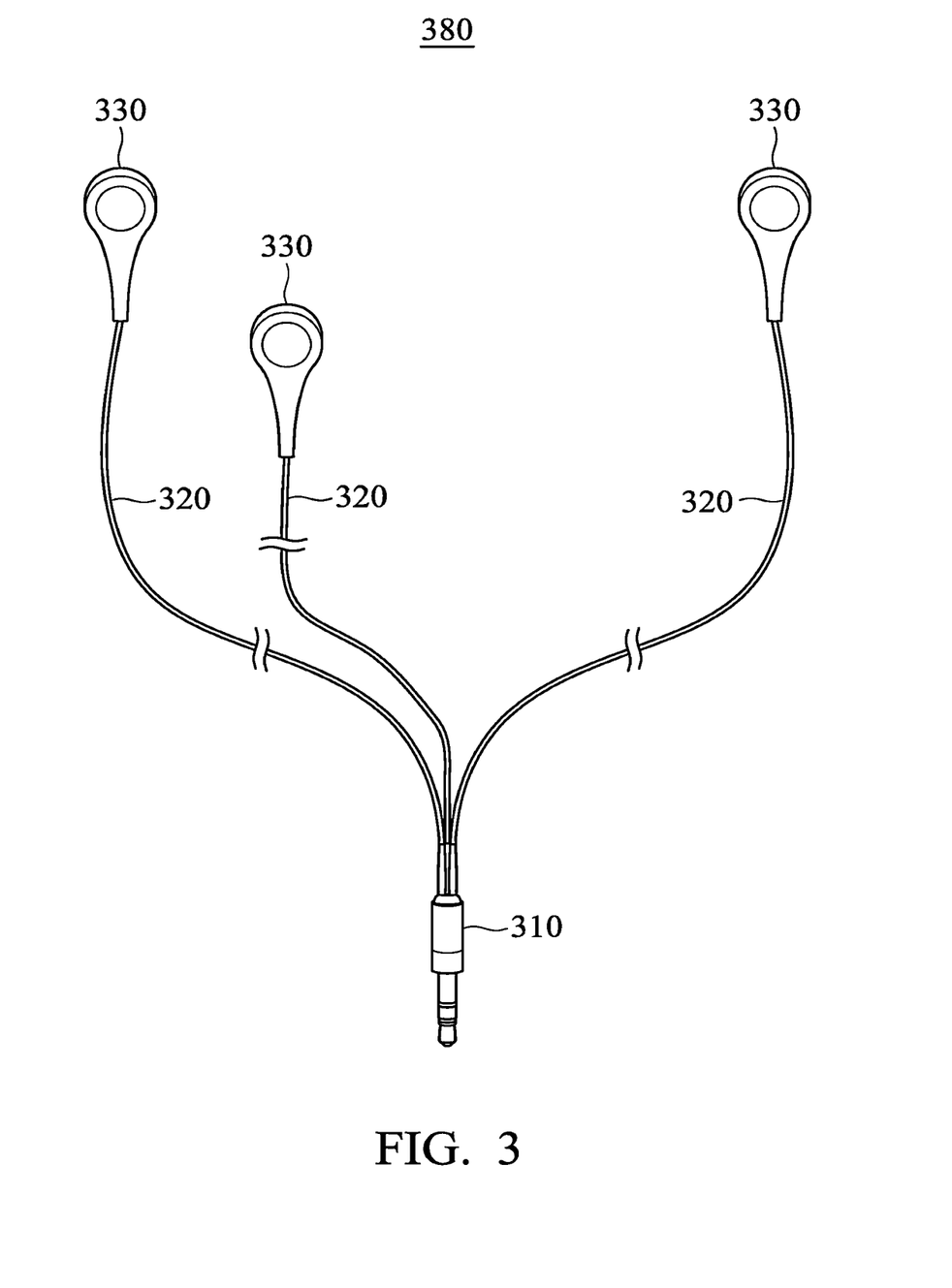
FIG. 3 is a perspective view of an external electrode according to an embodiment of the invention.

FIG. 3 is a perspective view of an external electrode 380 according to an embodiment of the invention. In the embodiment of FIG. 3, the aforementioned external sensor 180 is an external electrode 380. The external electrode 380 includes an earphone plug 310, one or more connection lines 320, and one or more sub-electrodes 330. The connection lines 320 are configured to respectively couple the sub-electrodes 330 to the earphone plug 310. For example, each of the sub-electrodes 330 may be a wet electrode with gel. The sub-electrodes 330 may be put on a human body (e.g., the user's chest) and be used to retrieve biological information therefrom. The retrieved biological information from the sub-electrodes 330 may be converted into the first biological signal SB1, and the first biological signal SB1 may be transmitted through the connector 110 and the switch element 140 to the biological signal processor 130. Since the external electrode 380 directly touches the human body and retrieves the biological information with little distortion, it can significantly increase the accuracy and sensitivity of the biological signal measurement and process.

Figure 4:
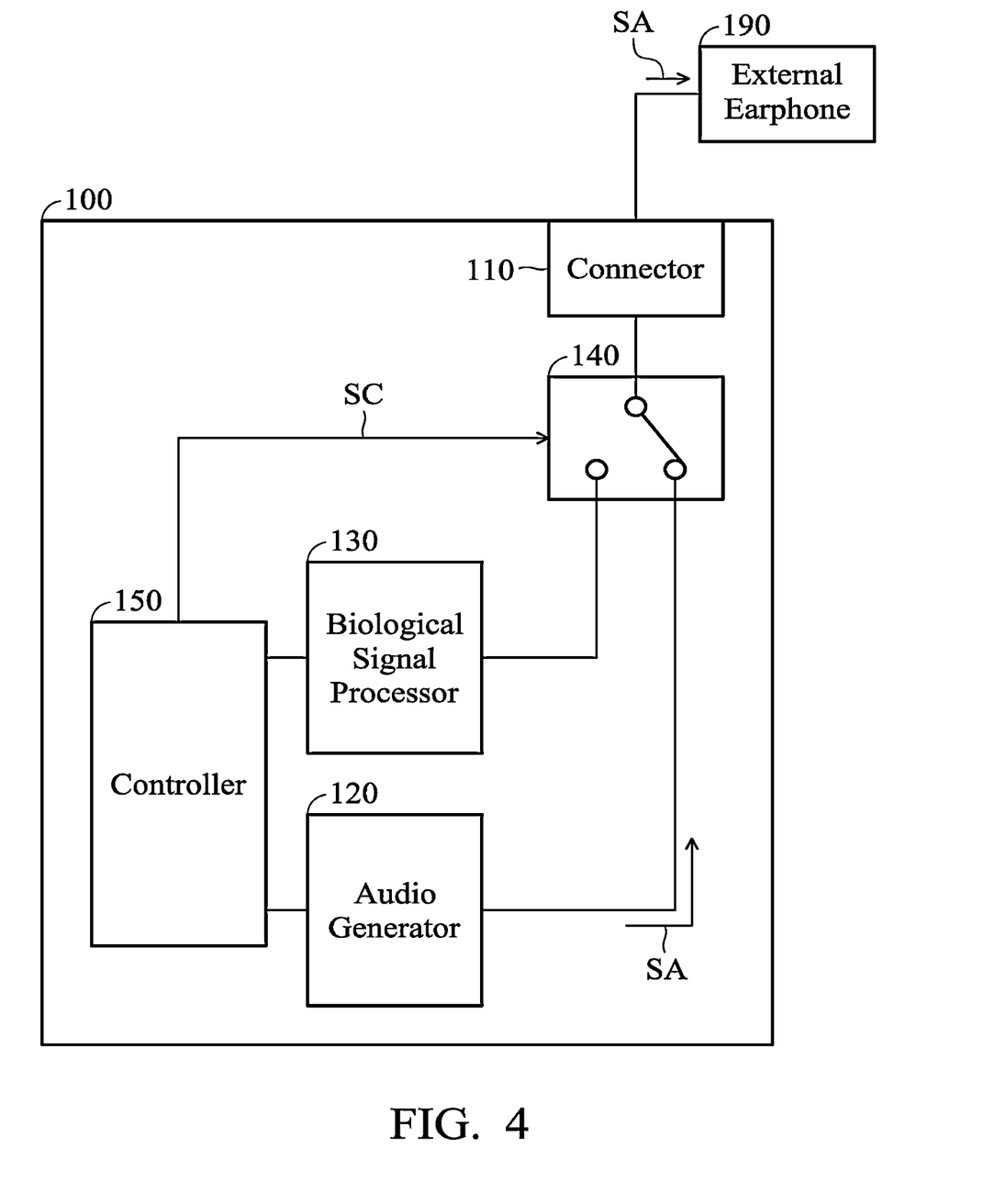
FIG. 4 is a diagram of a mobile device coupled to an external earphone according to an embodiment of the invention.

FIG. 4 is a diagram of the mobile device 100 coupled to an external earphone 190 according to an embodiment of the invention. In the embodiment of FIG. 4, the aforementioned external device 170 is an external earphone 190, and the external earphone 190 is coupled to the connector 110 of the mobile device 100. In the situation, no biological signal is transmitted to the connector 110. If the connector 110 does not receive any biological signal from the external earphone 190, the switch element 140 will change its switching operation and couple the connector 110 to the audio generator 120, instead of the biological signal processor 130. Then, the audio generator 120 may output an audio signal SA, and the audio signal SA may be transmitted through the switch element 140 and the connector 110 to the external earphone 190.

Figure 5:
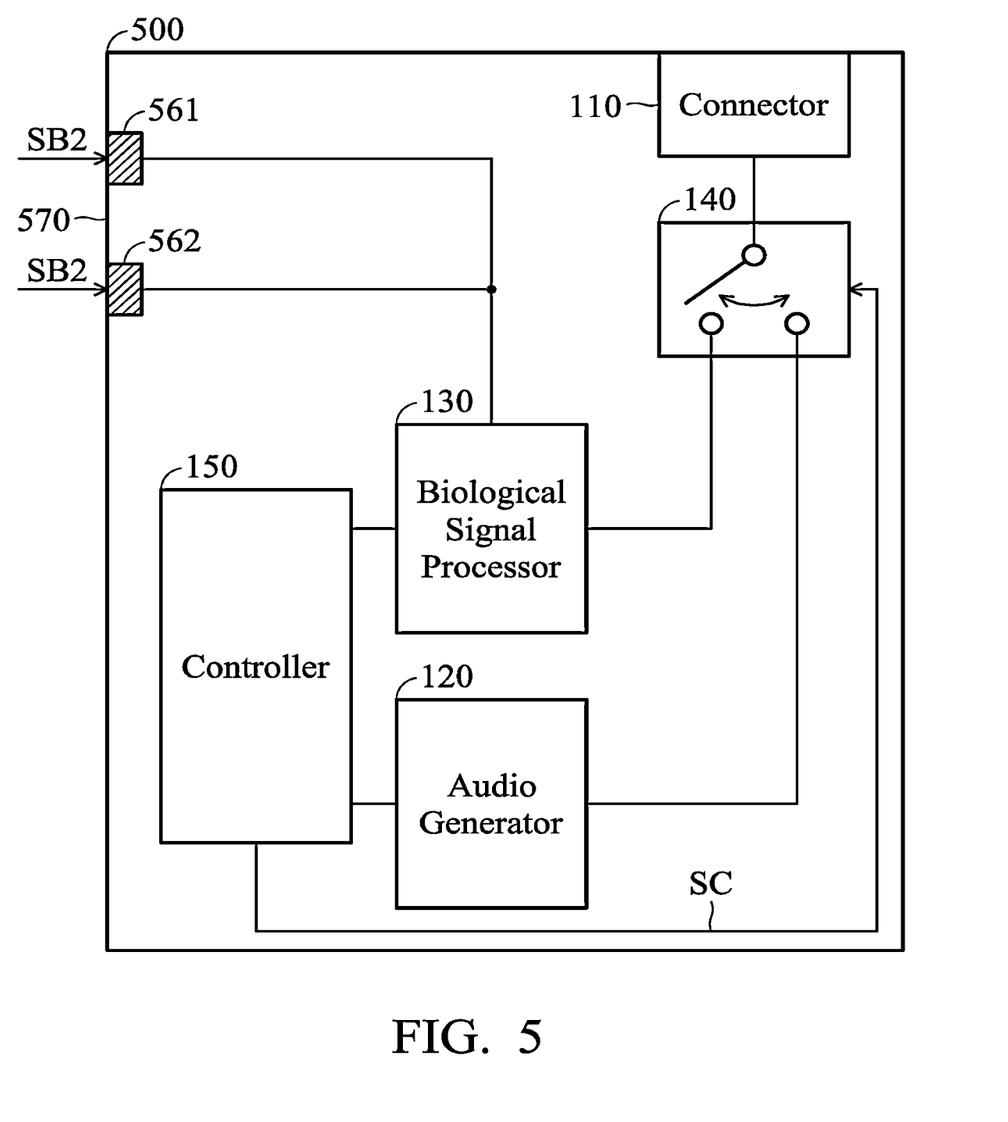
FIG. 5 is a diagram of a mobile device according to an embodiment of the invention.

FIG. 5 is a diagram of a mobile device 500 according to an embodiment of the invention. FIG. 5 is similar to FIG. 1. In the embodiment of FIG. 5, the mobile device 500 further includes at least two sensors 561 and 562, and a housing 570. The sensors 561 and 562 are embedded in the housing 570. For example, the sensors 561 and 562 may be made of a conductive material, and the housing 570 may be made of a nonconductive material. The sensors 561 and 562 are coupled to the biological signal processor 130. If no external device is coupled to the connector 110 or if the connector 110 does not receive any biological signal from the external device 170 (e.g., the external device 170 may be the external earphone 190), the biological signal processor 130 will try to receive and process a second biological signal SB2 from the sensors 561 and 562. Such a design provides an alternative sensing path, by which the mobile device 500 can retrieve biological information quickly and easily without using any external sensor. In some embodiments, the biological signal processor 130 has two input terminals, and it can selectively receive the first biological signal SB1 from the external device 170, or the second biological signal SB2 from the sensors 561 and 562. In alternative embodiments, the biological signal processor 130 has one input terminal, and an auxiliary switch element (not shown) is added and used to selectively transmit either the first biological signal SB1 from the external device 170, or the second biological signal SB2 from the sensors 561 and 562, to the biological signal processor 130. The auxiliary switch element may be controlled by the controller 150. It should be noted that the mobile device 500 may include three or more sensors in other embodiments although there are only two sensors 561 and 562 displayed in FIG. 5.

Figure 6A:
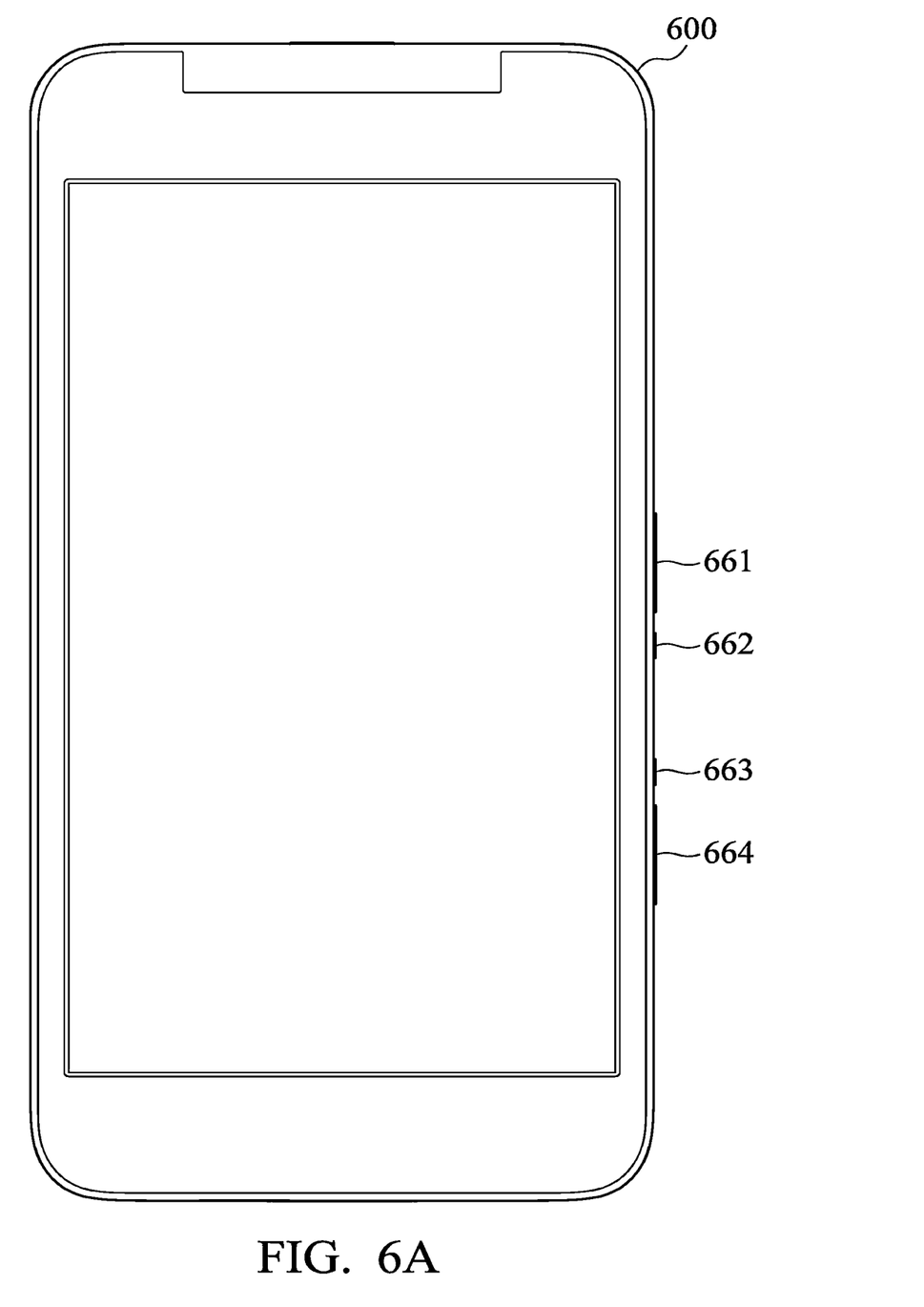
FIG. 6A is a top view of a mobile device according to an embodiment of the invention.
Figure 6B:
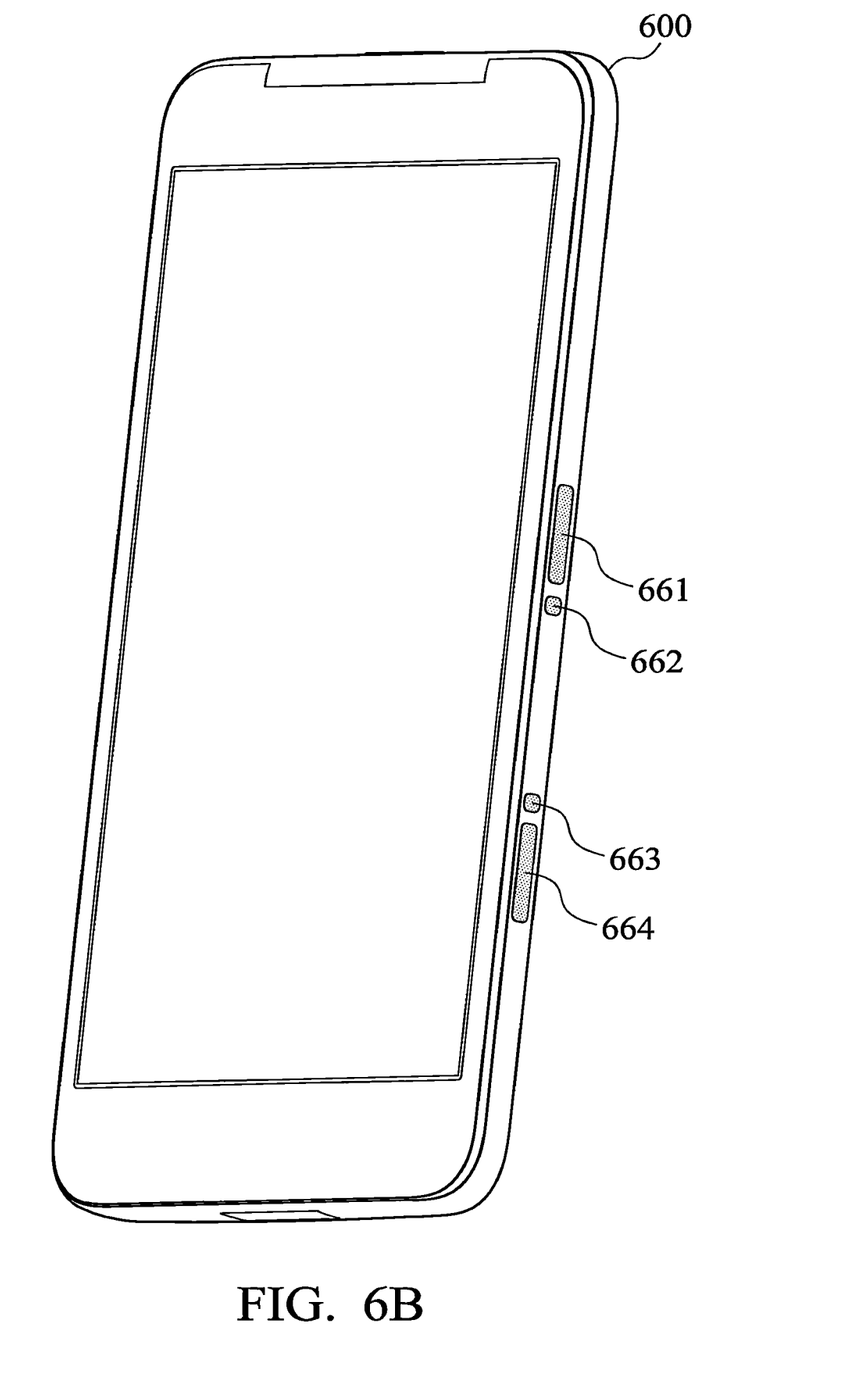
FIG. 6B is a perspective view of a mobile device according to an embodiment of the invention.

FIG. 6A is a top view of a mobile device 600 according to an embodiment of the invention. FIG. 6B is a perspective view of the mobile device 600 according to an embodiment of the invention. In the embodiment of FIG. 6A and FIG. 6B, the aforementioned sensors 561 and 562 are implemented with four electrodes 661, 662, 663, and 664. For example, each of the electrodes 661, 662, 663, and 664 may be a dry electrode without gel. The electrodes 661, 662, 663, and 664 may touch a portion of a human body (e.g., the user's fingers) and be used to retrieve biological information therefrom. The retrieved biological information from the electrodes 661, 662, 663, and 664 may be converted into the second biological signal SB2, and the second biological signal SB2 may be transmitted to the biological signal processor 130.

Figure 7:
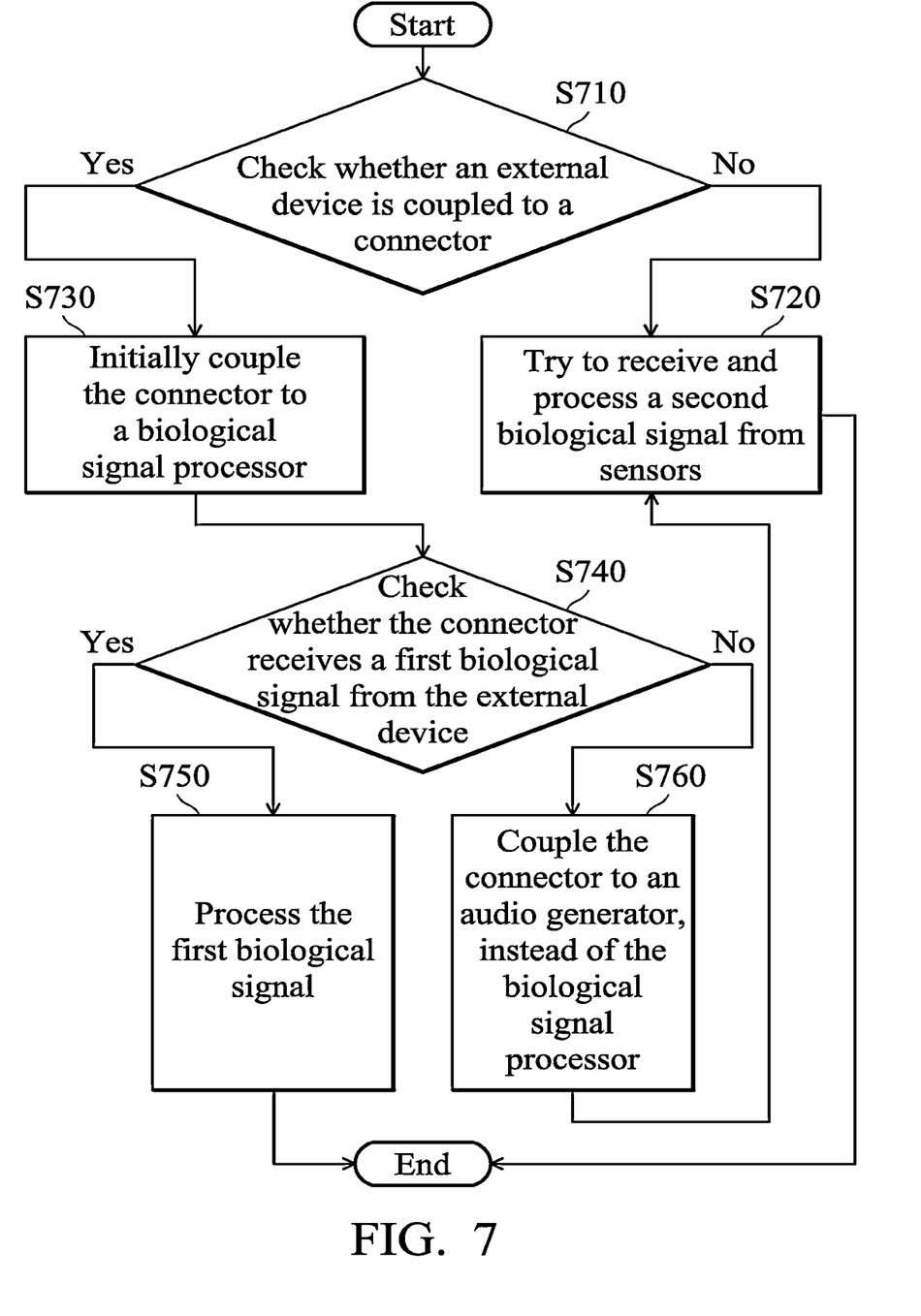
FIG. 7 is a flowchart of an operation method for operating a mobile device according to an embodiment of the invention.

FIG. 7 is a flowchart of an operation method for operating the mobile device 500 according to an embodiment of the invention. Please refer to FIG. 5 and FIG. 7 together. To begin, in step S710, the controller 150 checks whether the external device 190 is coupled to the connector 110. If not, in step S720, the biological signal processor 130 will try to receive and process the second biological signal SB2 from the sensors 561 and 562, and then the procedure will end. If so, in step S730, the switch element 140 will initially couple the connector 110 to the biological signal processor 130. In step S740, the controller 150 checks whether the connector 110 receives the first biological signal SB1 from the external device 190. If so, in step S750, the biological signal processor 130 will process the first biological signal SB1, and then the procedure will end. If not, in step S760, the switch element 140 will couple the connector 110 to the audio generator 120, instead of the biological signal processor 130. Next, the procedure may go back to step S720. The biological signal processor 130 will try to receive and process the second biological signal SB2 from the sensors 561 and 562, and then the procedure will end. In other embodiments, the operation method of FIG. 7 can be applied to the embodiments of FIGS. 1 to 6 with appropriate adjustments. For example, if the operation method of FIG. 7 is applied to the mobile device 100 of FIG. 1 (the sensors 561 and 562 are removed), only steps S730, S740, S750, and S760 may be performed.

Figure 8:
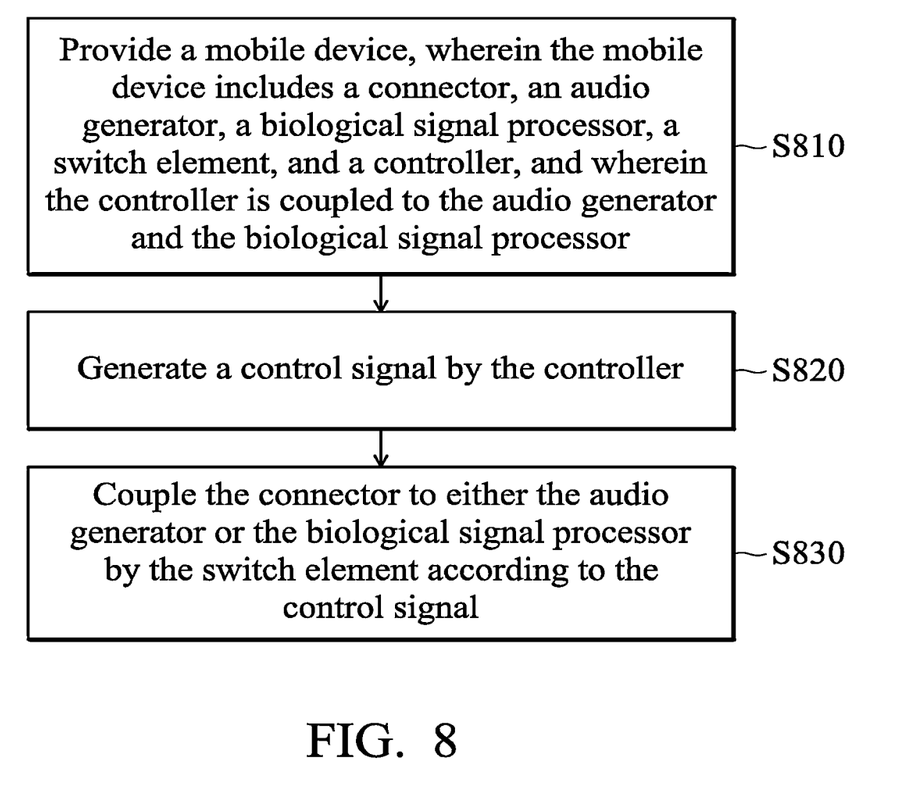
FIG. 8 is a flowchart of a control method according to an embodiment of the invention.

FIG. 8 is a flowchart of a control method according to an embodiment of the invention. To begin, in step S810, a mobile device is provided. The mobile device includes a connector, an audio generator, a biological signal processor, a switch element, and a controller. The controller is coupled to the audio generator and the biological signal processor. In step S820, a control signal is generated by the controller. Finally, in step S830, the connector is coupled to either the audio generator or the biological signal processor by the switch element according to the control signal. It should be noted that these steps may not be performed in order, and every feature of the embodiments of FIGS. 1 to 7 may be applied to the control method of FIG. 8.

The invention proposes a mobile device and a control method thereof. Because the mobile device selectively uses an external sensor, it can quickly and precisely retrieve biological information from a user. The external sensor can be coupled to a built-in connector of the mobile device, such as an earphone socket, so that no extra cost is required. A biological signal from the external sensor may be further processed and analyzed by a biological signal processor of the mobile device. Therefore, it becomes more convenient for the user to continuously and accurately monitor his/her state of health using the proposed mobile device and control method.

Note that the above voltages, currents, resistances, inductances, capacitances and other element parameters are not limitations of the invention. A designer can adjust these parameters according to different requirements. The mobile device and control method of the invention are not limited to the configurations of FIGS. 1-8. The invention may merely include any one or more features of any one or more embodiments of FIGS. 1-8. In other words, not all of the features displayed in the figures should be implemented in the mobile device and control method of the invention.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A mobile electronic device, comprising:
   a housing including a connector, an audio generator, a biological signal processor, a switch element and a controller;
   wherein the connector is configured to be coupled to an external sensor or an external device for collecting a first electrical biological signal indicating biological or physiologic information from a user's body;
   wherein the biological signal processor is configured for processing the first electrical biological signal;
   wherein the switch element has a first terminal and a second terminal, wherein the first terminal of the switch element is coupled to the connector, and the second terminal of the switch element is selectively coupled to either the audio generator or the biological signal processor according to a control signal; and
   wherein the controller is coupled to the audio generator and the biological signal processor, and is configured to generate the control signal for controlling a switching operation of the switch element;
   a plurality of sensors embedded in the housing and coupled to the biological signal processor, wherein the controller is configured to determine whether the external sensor or the external device is coupled to the connector and determine whether the external connector receives the first biological signal from the external sensor or the external device, and to initially control the switch element to couple the connector to the biological signal processor when the external sensor or the external device is determined to be coupled to the connector, then when the connector is determined not to receive the first electrical biological signal from the external sensor or the external device, control the switch element to couple the connector to the audio generator, and after the connector is coupled to the audio generator via the switch element, cause the biological signal processor to receive and process a second electrical biological signal from the plurality of sensors.

2. The mobile electronic device as claimed in claim 1, wherein if the connector receives the first electrical biological signal from the external sensor, the first electrical biological signal is configured to be transmitted through the switch element to the biological signal processor, such that the biological signal processor processes the first electrical biological signal.

3. The mobile electronic device as claimed in claim 1, wherein the plurality of sensors comprises electrodes.

4. A method for collecting an electrical biological signal indicating a biological or physiologic information from a user's body using a mobile electronic device, the mobile electronic device including: a housing including a connector, an audio generator, a biological signal processor, a switch element and a controller, wherein the connector is configured to be coupled to an external sensor or an external device for collecting a first electrical biological signal indicating biological or physiologic information from a user's body, wherein the biological signal processor is configured for processing the first electrical biological signal, wherein the switch element has a first terminal and a second terminal, wherein the first terminal of the switch element is coupled to the connector, and the second terminal of the switch element is selectively coupled to either the audio generator or the biological signal processor according to a control signal, and wherein the controller is coupled to the audio generator and the biological signal processor, and is configured to generate the control signal for controlling a switching operation of the switch element; a plurality of sensors embedded in the housing and coupled to the biological signal processor, the method comprising:
   the controller determining whether the external sensor or the external device is coupled to the connector and determining whether the external connector receives the first biological signal from the external sensor or the external device; and
   initially controlling the switch element to couple the connector to the biological signal processor when the external sensor or the external device is determined to be coupled to the connector, then when the connector is determined not to receive the first electrical biological signal from the external sensor or the external device, controlling the switch element to couple the connector to the audio generator, and after the connector is coupled to the audio generator via the switch element, causing the biological signal processor to receive and process a second electrical biological signal from the plurality of sensors.

* * * * *